(12) United States Patent
Chen et al.

(10) Patent No.: US 6,485,176 B1
(45) Date of Patent: Nov. 26, 2002

(54) INSPECTION SYSTEM WITH RHO-THETA X-RAY SOURCE TRANSPORT SYSTEM

(75) Inventors: Shih-Liang Chen, Yorba Linda; Jason T. McGaffey, San Juan Capistrano; Clifford S. Schuring, Dana Point, all of CA (US)

(73) Assignee: Photon Dynamics, Inc., San Jose, CA (US)

( * ) Notice: Subject to any disclaimer, the term of this patent is extended or adjusted under 35 U.S.C. 154(b) by 7 days.

(21) Appl. No.: 09/689,466

(22) Filed: Oct. 12, 2000

(51) Int. Cl.[7] .......................... H05G 1/02; G01N 23/04
(52) U.S. Cl. .......................... 378/193; 378/57; 378/58; 378/194; 378/197
(58) Field of Search ........................ 378/57, 58, 62, 378/63, 189, 193, 194, 197, 206, 25

(56) References Cited

U.S. PATENT DOCUMENTS

| | | | |
|---|---|---|---|
| 3,551,612 A | * 12/1970 | Guentner .................. 191/12 C |
| 4,139,776 A | * 2/1979 | Hellstrom .................... 378/25 |
| 4,926,452 A | * 5/1990 | Baker et al. .................. 378/22 |
| 5,010,254 A | * 4/1991 | Moore ........................ 250/551 |
| 5,388,136 A | * 2/1995 | Halliday et al. ............... 378/58 |
| 5,541,856 A | 7/1996 | Hammermeister .......... 378/196 |
| 6,088,424 A | * 7/2000 | Postlethwaite et al. ........ 378/63 |
| 6,301,327 B1 | * 10/2001 | Martens et al. ............... 378/57 |

* cited by examiner

Primary Examiner—Robert H. Kim
Assistant Examiner—Allen C. Ho
(74) Attorney, Agent, or Firm—Blakely, Sokoloff, Taylor & Zafman LLP

(57) ABSTRACT

Inspection systems with rho-theata x-ray source motion for inspection of populated printed circuit boards and the like. The inspection systems include a transport system for transporting articles to be inspected into and out of the inspection system. An x-ray source is mounted on a first radial translation system adjacent one side of the article to be inspected for translation along an axis parallel to the article to be inspected. The first translation system is rotatably mounted about an axis perpendicular to the article to be inspected so that the x-ray source may be positioned and moved anywhere within an area by proper coordination of the angle of rotation of the rotary transport system and the translational position of the first translational system. The exemplary embodiment disclosed also includes a second translational system supported on the first translational system for movement of the x-ray source in a direction parallel to the axis of rotation of the rotary transport system.

30 Claims, 4 Drawing Sheets

INSPECTION SYSTEM WITH RHO-THETA X-RAY SOURCE TRANSPORT SYSTEM

BACKGROUND OF THE INVENTION

1. Field of the Invention

The present invention relates to the field of x-ray inspection systems.

2. Prior Art

Inspection systems such as x-ray inspection systems and visual inspection systems are now frequently used for the inspection of various products. Of particular interest for the present invention is the inspection of products such as printed circuit boards having various electronic components physically and electrically connected thereto, generally referred to herein as populated boards or populated printed circuit boards. Such inspection, which frequently is at least partially automated, will detect missing components and solder bridges, and allow the evaluation of solder flow and bonding of device terminals to the printed circuit board. Certain features may readily be detected by a camera responsive to visible light (hereinafter referred to as the "visual image" or "visual camera"). Other features, particularly those which are shaded or sheltered by the devices themselves, may be detected by a camera responsive to the x-ray image created by the passing of x-rays through the printed circuit board and devices thereon from an x-ray source supported by some transport system on the side of the populated board opposite the camera (hereinafter referred to as the "x-ray image" or "x-ray camera"). In some cases, features of the populated board being inspected can be better inspected by misaligning the x-ray source and the x-ray camera so that the x-ray image is created by x-rays passing through the printed circuit board at an angle other than 90°. In still other instances, aspects of features can be best evaluated by combining the x-ray image and the visual image to extract information not readily discernable from either image alone.

U.S. Pat. No. 5,541,856 discloses an x-ray source transport system providing for x and y translation of the x-ray source. Such a system should perform well and has the advantage that device positions, etc. on the populated board are normally defined by x and y coordinates, not rho-theta coordinates. However, because such systems are generally processor controlled, conversion of inputs or commands from one coordinate system to another does not involve any additional cost or time delay. Also, coupling power and control signals through an x-y translation system, which in normal use frequently translates over most of its full range, can result in substantial design and reliability problems. By way of example, a single cable from a stationary part of the system to the x-ray source is subject to both abrasion and fatigue, requiring more maintenance than desired. Separate cabling for each translation system also presents its own problems in both design and reliability.

BRIEF SUMMARY OF THE INVENTION

Inspection systems with rho-theta x-ray source motion for inspection of populated printed circuit boards and the like are disclosed. The inspection systems include a transport system for transporting articles to be inspected into and out of the inspection system. An x-ray source is mounted on a first radial translation system adjacent one side of the article to be inspected for translation along an axis parallel to the article to be inspected. The first radial translation system is rotatably mounted about an axis perpendicular to the article to be inspected so that the x-ray source may be positioned and moved anywhere within an area by proper coordination of the angle of rotation of the rotary transport system and the radial translational position of the first translational system. The exemplary embodiment disclosed also includes a second translational system supported on the first translational system for movement of the x-ray source in a direction parallel to the axis of rotation of the rotary transport system. The use of the combination of radial translation and angular rotation for positioning of the x-ray source simplifies the coupling of power and control signals to the x-ray source and transport motors and controls.

DETAILED DESCRIPTION OF THE PREFERRED EMBODIMENT

Figure 1:
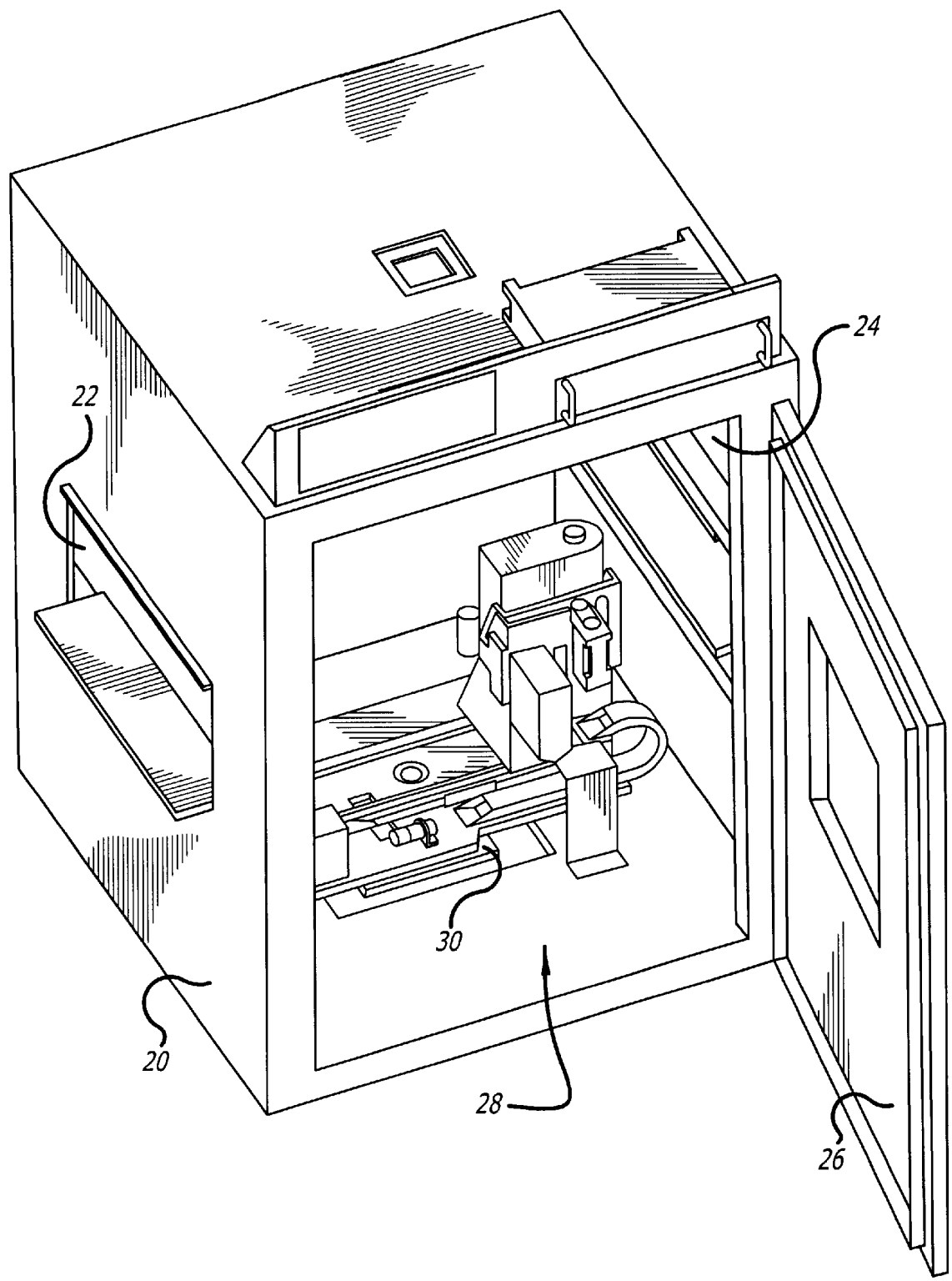
FIG. 1 is a perspective view of an exemplary inspection system in accordance with the present invention.

First referring to FIG. 1, a perspective view of an exemplary inspection system in accordance with the present invention may be seen. The inspection system generally includes an x-ray protective housing 20 having openings 22 and 24 for loading populated printed circuit boards onto, and removing the populated boards from, a transport system running through the housing 20. Such transport systems are well known, and generally comprise a conveyor-like structure at each side of the inspection system for supporting each populated board in alignment with the inspection system and translating the same into and out of the inspection system without obstructing the view of the devices on the populated board. In the system shown in FIG. 1, a door 26 is provided on one side of the system, or on both sides of the system if desired, to provide access for maintenance, if and when maintenance is required.

Figure 2:
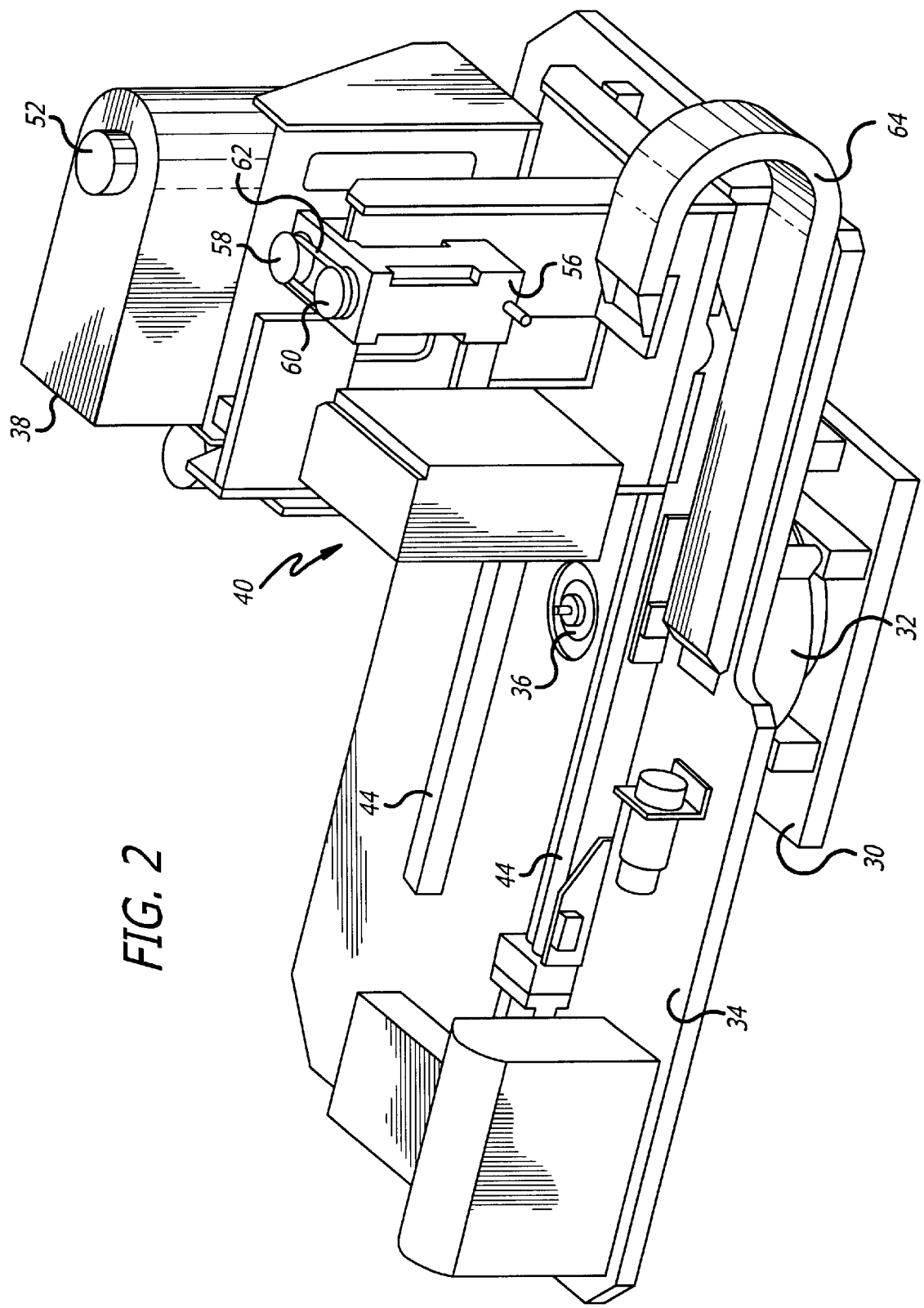
FIG. 2 is a perspective view of the transport system of the embodiment of FIG. 1 taken from one side thereof.
Figure 3:
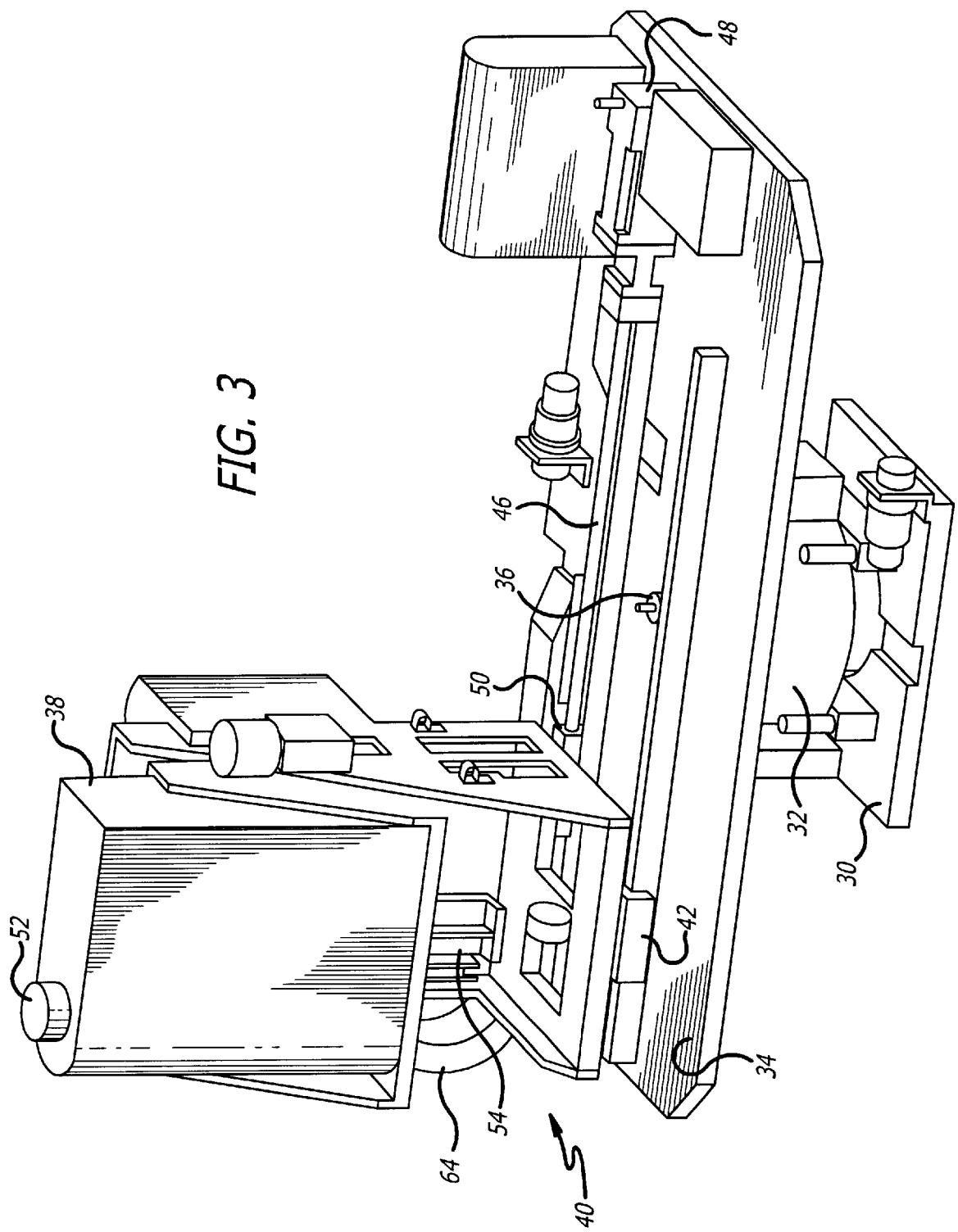
FIG. 3 is a perspective view of the transport system of the embodiment of FIG. 1 taken from the side of the transport system opposite that of FIG. 2.

The x-ray source transport system of the present invention, generally indicated by the numeral 28 in FIG. 1, may be seen on an expanded scale in FIGS. 2 and 3. FIG. 2 is a perspective view of the transport system taken from one side thereof, whereas FIG. 3 is a perspective view of the transport system taken from the side of the transport system opposite that of FIG. 2. The transport system is mounted on a mounting plate 30 which mounts within the enclosure 20 (FIG. 1) of the inspection system. Mounted on the mounting plate 30 within housing 32 is a relatively large, fine increment servo motor having a vertical axis, and supporting for rotation about its vertical axis a horizontal platform member 34. Also mounted above the servo motor, between a structure fixed to the mounting plate 30 and the platform member 34, is a slip-ring assembly 36 providing the required electrical coupling between the outside world and the devices mounted on or supported by the platform member. The servo motor and associated support bearings for the motor and platform 34 provide a first transport system for the x-ray source 38, specifically a rotary transport system capable of rotating through a full 360° and beyond without difficulty. In that regard, the slip-ring assembly provides simple and highly reliable electrical communication between the rotating assembly and the stationary assembly without any limitation on the rotary travel involved, and without risk of abrasion of a cable or fatigue of any conductors therein or connections thereto.

Mounted on the platform member 34 is a carriage assembly, generally indicated by the numeral 40, supported by ball bearing linear slides 42 on rail-like members 44. The carriage assembly 40 is positioned along the rail-like members 44 by the controlled rotation of a lead screw 46 by a servo motor 48, the lead screw engaging a ball bearing screw follower 50 rigidly mounted to the carriage assembly 40.

The x-ray source 38, when operating, provides point source x-ray emission through member 52. The radial transport system just described is configured to move the x-ray point source in a radial direction, including a position so that the point source may be aligned with the axis of the support bearings for the servo motor and platform 34 providing the angular transport system. In that regard, the radial transport system could be configured so as to pass equally on either side of the axis of the angular transport system. However, in the preferred embodiment, substantial radial motion of the carriage assembly is provided only in one radial direction relative to the carriage assembly, being limited in the other direction to being coincident with the axis of rotation of the angular transport system, or to only pass slightly beyond that axis. This has some design advantages over an x-y transport system, as it allows the positioning of the x-ray point source adjacent the outer side of the carriage assembly without limiting the ability of the x-ray source to approach any of the four walls of the inspection system enclosure. In comparison, it may be seen that if the x-ray source as shown in FIGS. 2 and 3 was used on an x-y translation system, the x-ray point source 52 could not closely approach at least one wall of the inspection system enclosure, either limiting the area being scanned or requiring a larger enclosure. In the preferred embodiment, the transport system of the present invention is positioned with the rotary axis of the transport system centered with respect to the rectangular area of motion of the x-ray source, with the circular area scanable by the rho-theta transport system being truncated to the desired rectangular scan area under software control by appropriate software limits on the useable rho-theta combinations.

Also note that, in effect, in both an x-y transport system of the prior art and the rho-theta transport system of the present invention, a first transport system is mounted on a second transport system. In the present invention, the radial transport system may be reasonably aligned with the center of gravity of the carriage assembly and will maintain such alignment independent of the theta position of the angular transport system. In an x-y transport system, however, while the first transport system will remain relatively well balanced, the second transport system on which it is mounted will be supporting and driving a highly cantilevered weight when the first transport system is at or near its limit of motion. In that regard, while the angular transport system of the present invention is only balanced when the radial transport system is one position, rotary bearings are easier to make rigid and should have substantially longer life and higher reliability than linear bearings operating with a cantilevered load. Since the radial motion is generally confined to one direction only, a diametrically opposed and complimentarily driven counterweight could be used to maintain balance in the carriage assembly, though this is not generally necessary and not incorporated in the preferred embodiment.

The carriage assembly 40 also includes a vertical ball bearing slide system 54 controlled by a servo motor 56 driving a lead screw through notched pulleys 58 and 60 by a toothed belt 62. This provides for vertical motion of the x-ray source that controls the extent of the field of view and the magnification in the x-ray image.

Electrical coupling between the platform member 34 and the assembly supported on the radial transport system is provided through a flat cable bundle 64, forming a rolling U-shaped electrical connection. The cable assembly 64 is comprised of a plurality of individual electrical cables positioned side by side within a flexible plastic enclosure. Rolling connections like this, though constructed in various ways, all generally have the electrical conductors substantially on the neutral axis of the cross-section.

Accordingly, on bending of the rolling U-shape and/or when straightening out, the metallic conductors are not subject to significant tensile forces and can easily be well confined to their elastic range by using wire having multiple strands of individual wires of suitable small diameter.

Figure 4:
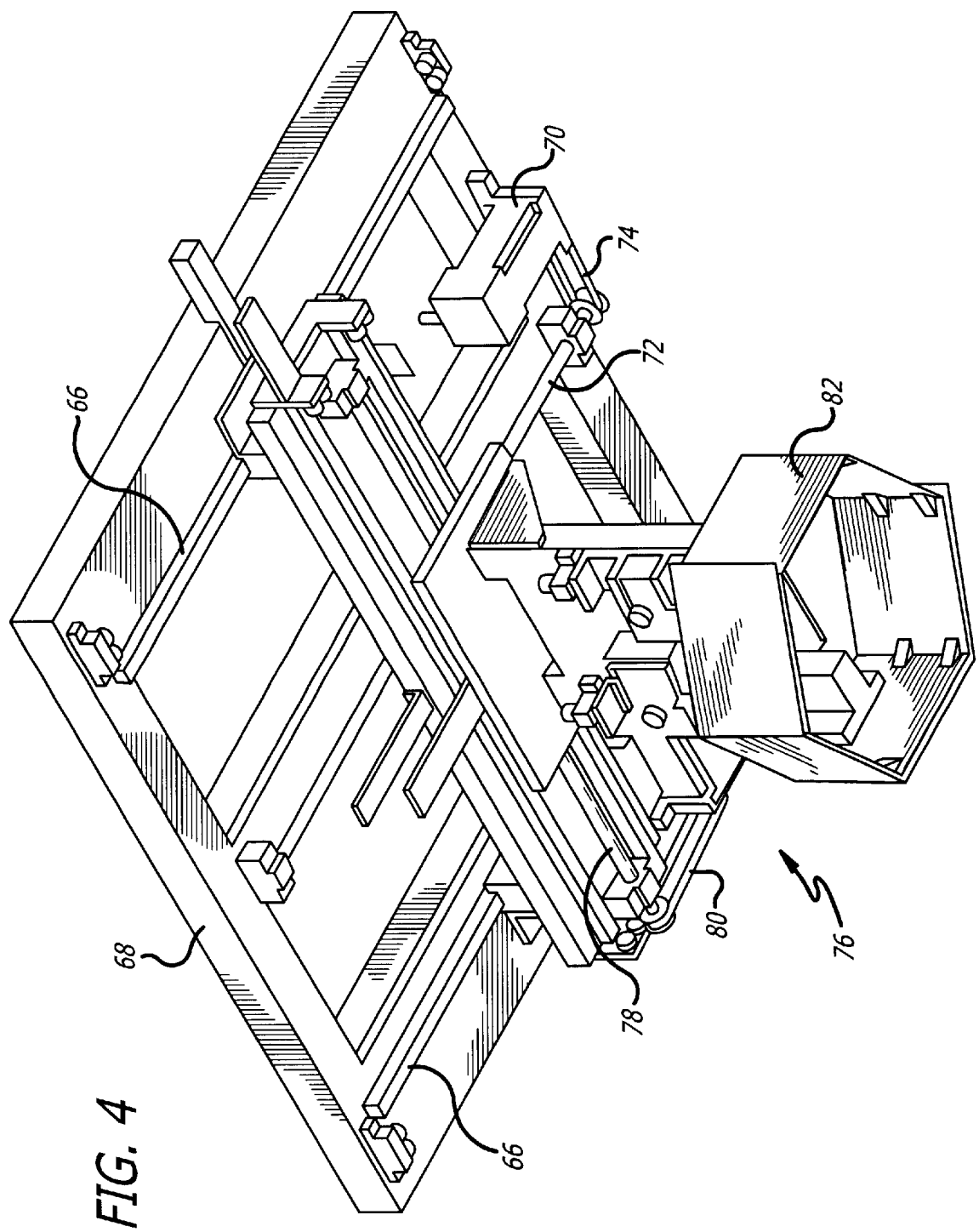
FIG. 4 is a perspective view of the camera arrangement at the top of the inspection system enclosure of the exemplary embodiment of FIG. 1.

Now referring to FIG. 4, a perspective view of the camera arrangement at the top of the inspection system enclosure may be seen. This structure is similar to that used in a prior art combined x-ray and visual inspection systems. The camera system is supported by a first ball bearing rail system by rails 66 supported on a top plate 68 and controllably driven along the rails by a servo motor 70, driving a lead screw 72 through a toothed belt system 74. A second orthogonal linear ball bearing support system provides motion along an orthogonal axis, that motion being controlled through a lead screw 78 driven through toothed belt system 80 by another servo motor. The camera system itself, generally indicated by the numeral 76, is comprised of a lighting system 82 and two cameras thereunder, one for sensing the visual image and one the x-ray image, the cameras generally being side by side so as to have optical axes which are spaced apart, though in relatively close proximity to each other. The use of the visual camera system, of course, does not depend upon the position of the x-ray source beneath the article to be inspected, but rather carries with it as part of the same assembly, the lighting system 82 for illuminating the article to be inspected. In a typical embodiment, a solid-state camera of ordinary construction may be used for the visual camera, with or without a zoom capability. The x-ray camera typically used includes an image intensifier on a camera of selected sensitivity for the purpose. Of course, to obtain the x-ray images desired, the x-ray camera will be transported on the x-y camera transport system on one side of the circuit board in coordination with the transport of the x-ray source by the rho-theta transport system on the opposite side of the circuit board. However, as pointed out before, since such systems are processor controlled, conversion from an x-y coordinate system to an rho-theta coordinate system is relatively trivial and presents no meaningful obstacle. In that regard, the x-y coordinate system of the inspection system may not have the same reference as a coordinate system specifying the location of the devices on the populated board to be inspected, so that some conversion is required anyway. Further, linear and angular corrections in transport system locations and/or image orientations may be required based upon the sensing of the actual orientation of the board to be inspected and/or the camera images, once the same passes into the inspection system. For all of these reasons, the use of an rho-theta transport system for inspecting components in locations known within an x-y coordinate system does not detract from the advantages of an rho-theta transport system, as more than ample coordinate conversion capabilities are present anyway for other purposes.

Thus while this invention has been described with reference to illustrative embodiments, this description is not intended to be construed in a limiting sense. Various modifications of the illustrative embodiments, as well as other embodiments of the invention which are apparent to persons skilled in the art to which the invention pertains are deemed to lie within the spirit and scope of the invention.

What is claimed is:

1. An x-ray inspection system comprising:

an x-ray source mounted on a radial translation system at a first side of an article to be inspected, the radial translation system controllably translating the x-ray source along a first axis;

the radial translation system being supported by an angular rotation system, the angular rotation system controllably rotating the radial translation system and the x-ray source mounted thereon about a second axis perpendicular to and intersecting the first axis; and, an x-ray camera mounted at a second side of an article to be inspected opposite the first side of an article to be inspected, the x-ray camera being mounted on an x-ray camera transport system controllable to move the x-ray camera about an area.

2. The x-ray inspection system of claim 1 wherein the radial translation system has a maximum range of motion of the x-ray source including from the axis of the angular rotation system to an outermost radial position.

3. The x-ray inspection system of claim 2 wherein the useable rho-theta combinations are limited to limit the motion of the x-ray source to within a rectangular area.

4. The x-ray inspection system of claim 1 wherein the x-ray camera transport system is an x-y transport system.

5. The x-ray inspection system of claim 1 further comprised of a slip-ring assembly providing electrical continuity between a non-rotatable structure and a rotatable structure of the angular rotation system.

6. The x-ray inspection system of claim 5 further comprised of a rolling cable assembly providing electrical continuity between a non-translatable structure and a translatable structure of the radial translation system.

7. The x-ray inspection system of claim 1 further comprised of a linear transport system between the x-ray source and the radial translation system, the linear transport system controllably translating the x-ray source along an axis parallel to the axis of the rotary transport system.

8. The x-ray inspection system of claim 1 further comprised of a visual image camera and visible lighting system mounted on the x-ray camera transport system.

9. An x-ray inspection system for inspecting printed circuit boards comprising:

an x-ray source mounted on a radial translation system at a first side of a printed circuit board to be inspected, the radial translation system controllably translating the x-ray source along a first axis parallel to the plane of a printed circuit board to be inspected;

the radial translation system being supported by an angular rotation system, the angular rotation system controllably rotating the radial translation system and the x-ray source mounted thereon about a second axis perpendicular to the plane of the printed circuit board to be inspected and perpendicular to and intersecting the first axis; and, an x-ray camera mounted at a second side of a printed circuit board to be inspected opposite the first side of a printed circuit board to be inspected, the x-ray camera being mounted on an x-ray camera transport system controllable to move the x-ray camera about an area parallel to a plane of the printed circuit board.

10. The x-ray inspection system of claim 9 wherein the radial translation system has a maximum range of motion of the x-ray source including from the axis of the angular rotation system to an outermost radial position.

11. The x-ray inspection system of claim 10 wherein the useable rho-theta combinations are limited to limit the motion of the x-ray source to within a rectangular area.

12. The x-ray inspection system of claim 9 wherein the x-ray camera transport system is an x-y transport system.

13. The x-ray inspection system of claim 9 further comprised of a slip-ring assembly providing electrical continuity between a non-rotatable structure and a rotatable structure of the angular rotation system.

14. The x-ray inspection system of claim 13 further comprised of a rolling cable assembly providing electrical continuity between a non-translatable structure and a translatable structure of the radial translation system.

15. The x-ray inspection system of claim 9 further comprised of a linear transport system between the x-ray source and the radial translation system, the linear transport system controllably translating the x-ray source along an axis parallel to the axis of the rotary transport system.

16. The x-ray inspection system of claim 9 further comprised of a visual image camera and visible lighting system mounted on the x-ray camera transport system.

17. A method of x-ray inspection comprising:

supporting an x-ray camera on a first transport system on a first side of the object to be inspected, the first transport system being controllable for movement of the x-ray camera about a first area;

supporting an x-ray source on a second transport system on a second side of the object to be inspected opposite the first side, the second transport system being an rho-theta transport system controllable for movement of the x-ray source about a second area; and, controlling the first and second transport systems so that the x-ray camera receives x-ray images of the object to be inspected.

18. The method of claim 17 wherein the first transport system is an x-y transport system.

19. The method of claim 17 wherein the x-ray source is so controlled in movement in a direction parallel to the rotary axis of the rho-theta transport system.

20. The method of claim 17 wherein the second area is a rectangular area, and the second transport system is limited motion of the x-ray source within the second area.

21. The method of claim 17 wherein electrical connections are made through a rotary axis of the rho-theta transport system by a slip-ring assembly and electrical connections are made through a radial transport system of the rho-theta transport system by a rolling cable assembly.

22. A method of x-ray inspection of a printed circuit board comprising:

supporting an x-ray camera on a first transport system on a first side of the printed circuit board to be inspected, the first transport system being controllable for movement of the ray camera about a first area parallel to the printed circuit board;

supporting an x-ray source on a second transport system on a second side of the printed circuit board to be inspected opposite the first side, the second transport system being an rho-theta transport system controllable for movement of the x-ray source about a second area parallel to the printed circuit board; and, controlling the first and second transport systems so that the x-ray camera receives x-ray images of the printed circuit board to be inspected.

23. The method of claim 22 wherein the first transport system is an x-y transport system.

24. The method of claim 22 wherein the x-ray source is also controlled in movement in a direction parallel to the rotary axis of the rho-theta transport system.

25. The method of claim 22 wherein the second area is a rectangular area, and the second transport system is limited to motion of the x-ray source within the second area.

26. The method of claim 22 wherein electrical connections are made through a rotary axis of the rho-theta transport system by a slip-ring assembly and electrical connections are made through a radial transport system of the rho-theta transport system by a rolling cable assembly.

27. An x-ray inspection system comprising:
an x-ray source mounted on a radial (rho)translation system at a first side of an article to be inspected, the radial translation system controllably translating the x-ray source along a first axis;
the radial translation system being supported by an angular (theta) rotation system, the angular rotation system controllably rotating the radial translation system and the x-ray source mounted thereon about a second axis perpendicular to and intersecting the first axis; and,
an x-ray camera mounted at a second side of an article to be inspected opposite the first side of an article to be inspected, the x-ray camera being mounted on an x-ray camera transport system controllable to move the x-ray camera about an area;
the useable rho-theta combinations being limited to limit the motion of the x-ray source to within an area to scan an area of the article to be inspected without movement of the article to be inspected.

28. An x-ray inspection system for inspecting printed circuit boards comprising:
an x-ray source mounted on a radial (rho) translation system at a first side of a printed circuit board to be inspected, the radial translation system controllably translating the x-ray source along a first axis parallel to the plane of a printed circuit board to be inspected;
the radial translation system being supported by an angular rotation system, the angular rotation system controllably rotating the radial translation system and the x-ray source mounted thereon about a second axis perpendicular to the plane of the printed circuit board to be inspected and perpendicular to and intersecting the first axis; and,
an x-ray camera mounted at a second side of a printed circuit board to be inspected opposite the first side of a printed circuit board to be inspected, the x-ray camera being mounted on an x-ray camera transport system controllable to move the x-ray camera about an area parallel to a plane of the printed circuit board;
the useable rho-theta combinations being limited to limit the motion of the x-ray source to within an area to scan an area of the printed circuit board to be inspected without movement of the printed circuit board.

29. A method of x-ray inspection comprising:
supporting an x-ray camera on a first transport system on a first side of the object to be inspected, the first transport system being controllable for movement of the x-ray camera about a first area;
supporting an x-ray source on a second transport system on a second side of the object to be inspected opposite the first side, the second transport system being a rho-theta transport system controllable for movement of the x-ray source about a second area; and,
controlling the first and second transport systems so that the x-ray camera receives x-ray images of different parts of the object to be inspected without movement of the object to be inspected.

30. A method of x-ray inspection of a printed circuit board comprising:
supporting an x-ray camera on a first transport system on a first side of the printed circuit board to be inspected, the first transport system being controllable for movement of the x-ray camera about a first area parallel to the printed circuit board;
supporting an x-ray source on a second transport system on a second side of the printed circuit board to be inspected opposite the first side, the second transport system being an rho-theta transport system controllable for movement of the x-ray source about a second area parallel to the printed circuit board; and,
controlling the first and second x-ray systems so that the x-ray camera receives x-ray images of the printed circuit board to be inspected; and,
controlling the first and second transport systems so that the x-ray camera receives x-ray images of different parts of the printed circuit board to be inspected without movement of the printed circuit board.

* * * * *